(12) United States Patent
Omar

(10) Patent No.: US 6,560,550 B2
(45) Date of Patent: May 6, 2003

(54) DEVICE AND METHOD FOR INDIRECT MEASUREMENT OF PHYSICAL PROPERTY OF ROCK AND SOIL

(75) Inventor: Husaini Bin Omar, Selangor Darul Ehsan (MY)

(73) Assignee: Universiti Putra Malaysia (MY)

( * ) Notice: Subject to any disclaimer, the term of this patent is extended or adjusted under 35 U.S.C. 154(b) by 3 days.

(21) Appl. No.: 09/812,881

(22) Filed: Mar. 20, 2001

(65) Prior Publication Data

US 2001/0032055 A1 Oct. 18, 2001

(30) Foreign Application Priority Data

Mar. 20, 2000 (MY) ...................................... PI 20001081

(51) Int. Cl.⁷ .................................................. G01L 1/00
(52) U.S. Cl. ............................. 702/42; 702/47; 702/50; 702/104; 73/32 R; 73/861.03
(58) Field of Search .............................. 702/42, 47, 50, 702/104, 137, 138; 73/32 R, 861.03

(56) References Cited

PUBLICATIONS

Omega The Pressure Strain and Force Handbook, vol.29 (pp. B3–B8, B61–B64, B69–B74, B77–B78 and B92–B94, .*

Campanella and Hitchman, *Can. Geotech. J.* 27: 167–176 (1990).

Strydom and Sanders, *ICSMFE* 13:129–134 (1994).

* cited by examiner

*Primary Examiner*—John Barlow
*Assistant Examiner*—Hien Vo
(74) *Attorney, Agent, or Firm*—Wolf, Greenfield & Sacks, P.C.

(57) ABSTRACT

The present invention relates to a device and method for measurement of tensile strength of materials, especially for indirectly measuring the tensile strength of weak rock and hard soil. The probe of the measuring device comprises a cylindrical body with an expandable flexible membrane designed to apply a uniform pressure to the walls of a cavity, such as a bore hole. There is no need to cut a core specimen to a particular shape for measurement, thus making it an attractive option for measurement of weakly bonded rock and hard soil.

18 Claims, 2 Drawing Sheets

DEVICE AND METHOD FOR INDIRECT MEASUREMENT OF PHYSICAL PROPERTY OF ROCK AND SOIL

RELATED APPLICATIONS

This application claims priority under 35 U.S.C. §119 from Malaysian patent application serial number PI 20001081, filed Mar. 20, 2000.

TECHNICAL FIELD OF THE INVENTION

The present invention generally relates to a device and method for measurement of tensile strength of materials, especially for indirectly measuring tensile strength of weak rock and hard soil.

BACKGROUND OF THE INVENTION

Generally, when measurements of tensile strength of rock and soil are made, there is a need to cut core specimens to a particular form to enable measurement using the appropriate equipment. This is sometimes difficult to achieve, time-consuming and costly. Further, it is necessary to transport bulky and heavy equipment to the site for measurement purposes.

To overcome the above-mentioned problems, there arise a need to provide a measuring device that is reliable, simple to use, small, light, portable and inexpensive. This is the subject of the present invention. In the present invention, the inventor proposes a measuring device for indirectly measuring tensile strength of weak rock and hard soil which is reliable, simple to use, portable and can even be used in the laboratory.

SUMMARY OF THE INVENTION

Accordingly, it is the primary object of the present invention to provide a measuring device that is capable of indirectly measuring the tensile strength of rock and soil. It is also another object of the present invention to provide a measuring device that is reliable, inexpensive and convenient to use.

This and other objectives of the present invention is accomplished by, A measuring device for indirectly measuring tensile strength of rock or soil, comprising:
  a probe for applying pressure to said rock or soil, said probe comprising:
    a main body (1c), said main body (1c) having a fluid passageway,
    a membrane (1e) enclosing said main body (1c),
    a head connector (1a) for fastening said membrane (1e) to upper portion of said main body (1c),
    a tail (1d) for fastening said membrane (1e) to bottom portion of said main body (1c), and
    a ring (1b) for holding said membrane (1e) to said upper and bottom portion of said main body (1c);
  a control unit comprising:
    a pump means for supplying pressurized fluid into said main body (1c); and
    a computer means for computing tensile strength of said rock or soil.

The measuring device according to the present invention provides a reliable, simple and convenient means for indirect measurement of tensile strength of materials, overcoming difficulties mentioned above and providing an inexpensive means of measurement.

BRIEF DESCRIPTION OF THE DRAWINGS

Other aspects of the present invention and their advantages will be discerned after studying the detailed description in conjunction with the accompanying drawings in which.

DETAILED DESCRIPTION OF THE DRAWINGS

Figure 1:
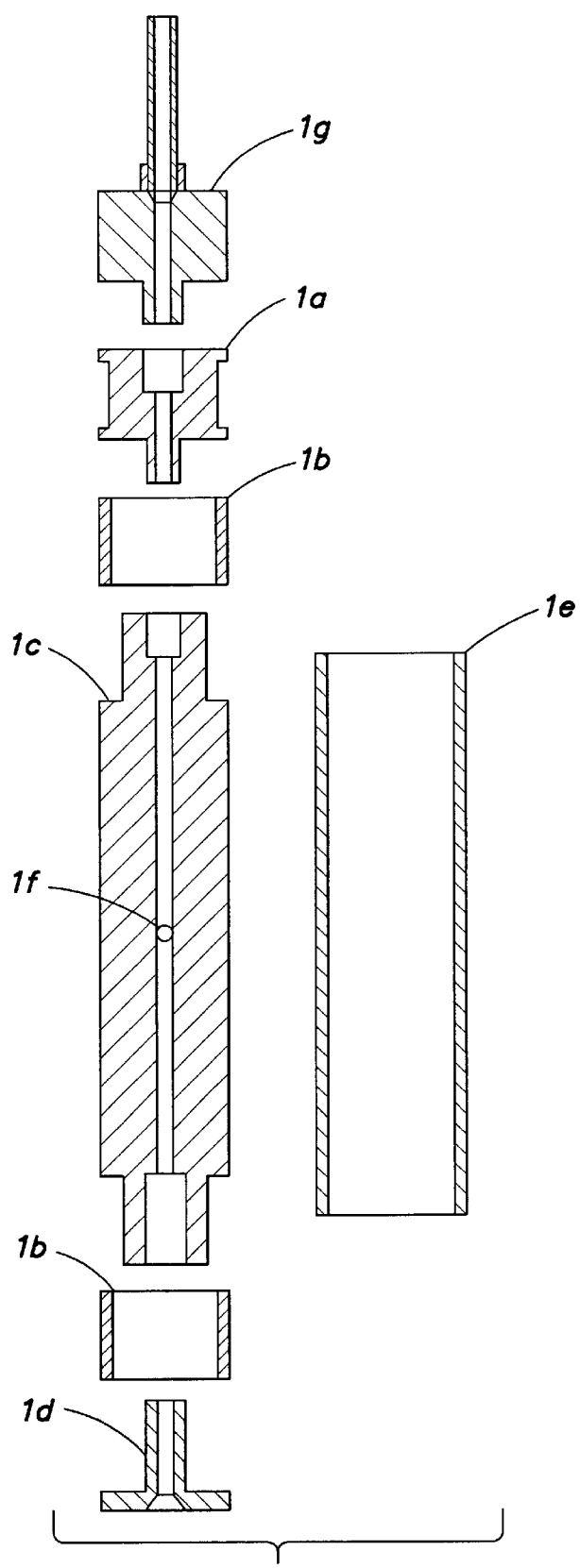
FIG. 1 is a schematic representation of a preferred embodiment of the measuring device according to the present invention.

Referring now to FIG. 1 showing a preferred embodiment of the measuring device according to the present invention, which comprises a head connector (1a), ring (1b), a main body (1c), a tail (1d) and a membrane (1e). The head connector (1a) connects the main body (1c) to tubing (1g) which is attached to a control unit. The ring (1b) is a special clip which secures the membrane (1e) to the main body (1c). The main body (1c) represents a major part of the measuring device and it is open at one end with a hole in the mid-portion of the body (1f). The tail (1d) is located at the lower end of the probe and it fastens a membrane (1e) at the lower end of the probe.

The probe is a cylinder which is preferably made from stainless steel and preferably the inner diameter being 2 mm and the outer diameter being 12 mm. The overall dimension is preferably 74 mm in length and 12 mm in diameter, and a measuring length of 40 mm. The membrane (1e) is preferably made from rubber with high elasticity, and preferably the thickness of the membrane is between 0.5 mm to 1.0 mm.

Figure 2:
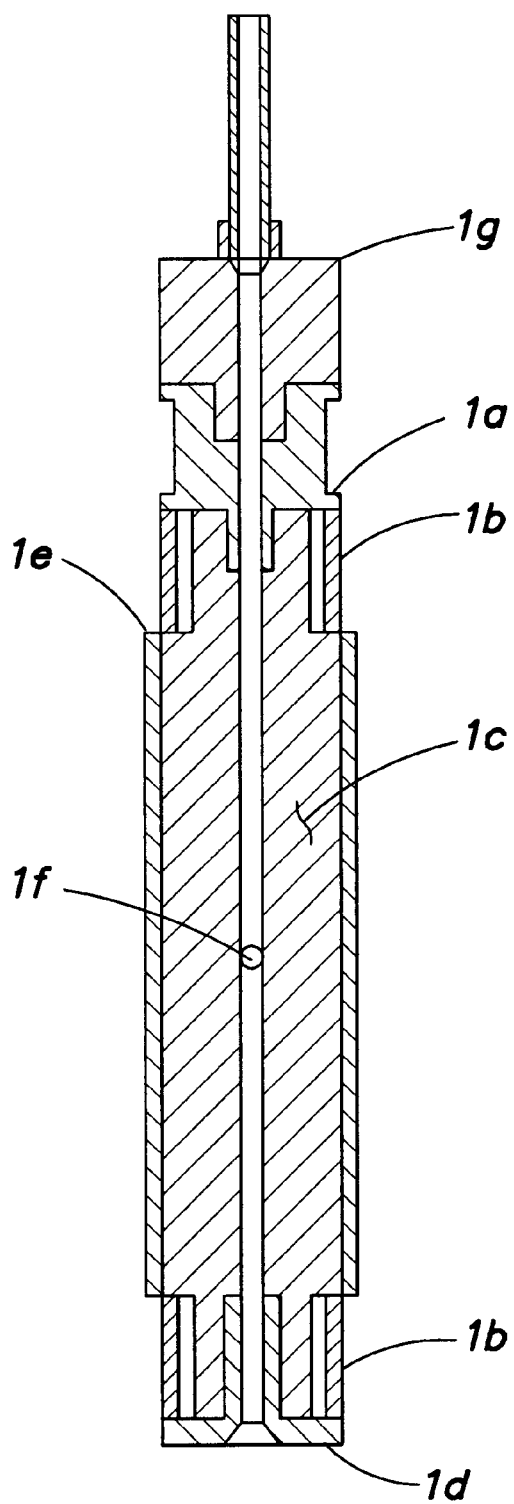
FIG. 2 illustrates the assembled measuring device.

Referring now to FIG. 2 showing the assembled measuring device, the set-up for testing a material using the measuring device according to the present invention, comprises inserting the probe into the measured material and connecting the probe via the head connector (1a) to a control unit comprising a pump and a computer, by means of stainless steel tubing.

Procedures for Testing Using the Measuring Device

The measuring device according to the present invention is for indirect measurement of tensile strength of weak rock, hard soil and other similar materials. There is no need to cut core specimens to a particular shape for testing, thus making it an attractive and convenient option of measuring the tensile strength of weakly bonded rock and hard soil. It is necessary to pre-drill a small hole for insertion of the measuring device. Once inserted, the device is inflated using a suitable fluid until the test specimen fails, while volume and pressure are monitored at the control unit.

Calibration

Calibration of the measuring device is an essential operation required for obtaining the corrected pressure-volume curve. It is calibrated before conducting a test. The calibration must be carried out correctly so that the true response of the weak rock and hard soil can be determined from the test.

Calibration is undertaken by inflating the membrane in air to obtain the membrane resistance or also known as membrane correction. The membrane is inflated by injecting water into the measuring device with constant volume (e.g. 100 mm$^3$), and the pressures were recorded. The measuring device is placed upright so that it works in the same sense, as it will in the real test. The calibrations are carried out at room temperature because the properties of the membrane and the control unit are temperature dependent. The time taken for every reading is one-minute intervals, same as applied in the real test.

For the line calibration, it is undertaken by inserting the measuring device into a close-fitting thick-walled rigid steel cylinder, this is important to check for any leakage of the system and also for the satisfactory de-airing of the measuring device. The membrane was expanded against the wall of the thick-walled cylinder and the pressure raised in increments until the maximum anticipated working pressure is reached. Each increment of pressure is held for one minute. Because of the space between the measuring device and the steel tube, and the resistance of the membrane, it takes a certain volume and pressure to inflate the measuring device into contact with the steel tube. As a general rule, the calibration test should be conducted every time before using the measuring device.

Testing of Materials

The measuring device test is stress controlled. Fixed pressure increments are applied. The increment of pressure is estimated until failure occurs of up to the pressure limit of the control unit, so it depends on the strength of the materials.

For testing, the probe is installed in the pre-drilled hole in a piece of rock or in hard soil. The hole was drilled vertically in a piece of core, the probe is connected by steel tubing to the control unit, where pressure is applied and volume changes (in $mm^3$) are recorded. The change in volume is recorded between 30 seconds and 60 seconds.

At the beginning of the test, the increments of pressure are 25 kPa intervals up to 100 kPa and each pressure is maintained for one minute. After 100 kPa, the increment of pressure is increased by 50 to 100 kPa depending on suitable pressure, until complete failure of the specimen. Failure was sudden and occurred without warning. It is important to keep a close watch on the rate of volume change during testing. It is recommended to increase the pressure by 50 or 100 kPa for safety and to achieve a better result.

While the preferred embodiments of the present invention have been described, it should be understood that various changes, adaptations and modifications may be made thereto. It should be understood, therefore, that the invention is not limited to details of the illustrated invention shown in the figures and that variations in such minor details will be apparent to one skilled in the art.

I claim:

1. A measuring device for indirectly measuring tensile strength of rock or soil, comprising:
    a probe for applying pressure to said rock or soil, said probe comprising:
        a main body (1c), said main body (1c) having a fluid passageway,
        a membrane (1e) enclosing said main body (1c),
        a head connector (1a) for fastening said membrane (1e) to upper portion of said main body (1c),
        a tail (1d) for fastening said membrane (1e) to bottom portion of said main body (1c), and
        a ring (1b) for holding said membrane (1e) to said upper and bottom portion of said main body (1c);
    a control unit comprising:
        a pump means for supplying pressurized fluid into said main body (1c); and
        a computer means for computing tensile strength of said rock or soil.

2. The measuring device according to claim 1, characterized in that the probe comprises a cylinder which forms the main body (1c).

3. The measuring device according to claim 2, characterized in that the cylinder of the probe is made from stainless steel.

4. The measuring device of claim 1, characterized in that the membrane (1e) has high elasticity, is expandable and flexible.

5. The measuring device according to claim 4, characterized in that the membrane (1e) is made from rubber.

6. The measuring device according to claim 1, characterized in that the rings (1b) for securing a membrane (1e) to the main body (1c) are in the form of special clips.

7. The measuring device according to claim 1, characterized in that the computer means indirectly measures tensile strength of a material by means of measurement of applied pressure until failure occurs or up to the pressure limit of a control unit.

8. The measuring device according to claim 1, characterized in that the device is small, light and portable.

9. The measuring device according to claim 1, characterized in that the probe can be inserted into a small opening for measurement purpose without need to cut core specimen to a particular shape.

10. A method for indirect measurement of tensile strength of materials, comprising: inserting the measuring device of claim 1 into said materials and measuring the tensile strength of said materials.

11. A method for indirect measurement of tensile strength of materials, comprising: inserting the measuring device of claim 2 into said materials and measuring the tensile strength of said materials.

12. A method for indirect measurement of tensile strength of materials, comprising: inserting the measuring device of claim 3 into said materials and measuring the tensile strength of said materials.

13. A method for indirect measurement of tensile strength of materials, comprising: inserting the measuring device of claim 4 into said materials and measuring the tensile strength of said materials.

14. A method for indirect measurement of tensile strength of materials, comprising: inserting the measuring device of claim 5 into said materials and measuring the tensile strength of said materials.

15. A method for indirect measurement of tensile strength of materials, comprising: inserting the measuring device of claim 6 into said materials and measuring the tensile strength of said materials.

16. A method for indirect measurement of tensile strength of materials, comprising: inserting the measuring device of claim 7 into said materials and measuring the tensile strength of said materials.

17. A method for indirect measurement of tensile strength of materials, comprising: inserting the measuring device of claim 8 into said materials and measuring the tensile strength of said materials.

18. A method for indirect measurement of tensile strength of materials, comprising: inserting the measuring device of claim 9 into said materials and measuring the tensile strength of said materials.

\* \* \* \* \*